United States Patent [19]

Berthe et al.

[11] Patent Number: 5,565,597
[45] Date of Patent: Oct. 15, 1996

[54] PROCESS FOR PREPARING THIOCYANOALKYL ESTERS OF (METH)ACRYLIC ACID

[75] Inventors: Marie-Christine Berthe, Vandoeuvre Les Nancy; Paul Caubere, Nancy; Yves Fort, Vandoeuvre Les Nancy, all of France

[73] Assignee: Atochem, Paris la Defense, France

[21] Appl. No.: 411,151

[22] Filed: Mar. 27, 1995

Related U.S. Application Data

[62] Division of Ser. No. 214,480, Mar. 17, 1994, Pat. No. 5,468,856, which is a division of Ser. No. 725,810, Jul. 9, 1991, Pat. No. 5,332,850.

[30] Foreign Application Priority Data

Jul. 9, 1990 [FR] France .................................. 90 08698

[51] Int. Cl.$^6$ .................................. C07C 331/04
[52] U.S. Cl. ........................ 558/12; 558/14; 526/261; 526/266; 526/288; 544/219
[58] Field of Search ........................ 558/12, 14

[56] References Cited

U.S. PATENT DOCUMENTS 3,743,669   7/1973   Hillman et al. .................... 558/451

FOREIGN PATENT DOCUMENTS

| 7-220201 | 6/1972 | Japan | 544/219 |
| 2-292774 | 12/1987 | Japan | 544/219 |
| 0546612 | 3/1974 | U.S.S.R. | 544/219 |

OTHER PUBLICATIONS

Chem. Abs., Registry Number Index, Columbus, OH, Composes No. 76392–31–9, 53397–61–8, 1972–1976.
Chem. Abs., vol. 83, 1975, p. 428, Columbus, OH, Solodkin: "Luminescence characteristics of electroluminescent layers based on binders with . . . ".
Chem. Abs., vol. 81, 1974, p. 389, Columbus, OH.
Chem. Abs., 9th Collective Idx. 1972–1976, p. C7H9N02S, Columbus, OH, "2–propmoic acid–2–methyl,2,thiocyanato ethyl ester homopolymer".
Synth. Commun., 22(4), 617–28, 1992.
"A New Synthesis of Thiocyanatoalkyl (Meth)acrylic esters", Berthe et al., *Synthetic Communications*, vol. 22(4), pp. 617–628, 1992.

*Primary Examiner*—Yogendra N. Gupta
*Attorney, Agent, or Firm*—Millen, White, Zelano, & Branigan, P.C.

[57] ABSTRACT

A process for the preparation of an acrylic or methacrylic compound of formula (I):

$$CH_2=C\begin{matrix}R\\ \\C-O-(CH_2)_n-SCN\\\parallel\\O\end{matrix} \quad (I)$$

wherein R is a hydrogen atom or methyl and n is an integer ranging from 2 to 20 inclusive, comprising reacting a halogeno-n-alkyl acrylate or methacrylate of the formula:

$$CH_2=C\begin{matrix}R\\ \\C-O-(CH_2)_n-X\\\parallel\\O\end{matrix} \quad (III)$$

in which n is as defined above and X is a halogen atom, with a thiocyanate salt in an organic solvent and in the presence of an effective phase-transferring amount of at least one phase-transfer agent.

7 Claims, No Drawings

PROCESS FOR PREPARING THIOCYANOALKYL ESTERS OF (METH)ACRYLIC ACID

This is a divisional application of Ser. No. 08/214,480 filed Mar. 17, 1994, now U.S. Pat. No. 5,468,856, which is a divisional application of Ser. No. 07/725,810 filed Jul. 9, 1991, which issued as U.S. Pat. No. 5,332,850 on Jul. 26, 1994.

BACKGROUND OF THE INVENTION

This invention relates to the synthesis of new acrylic and methacrylic compounds carrying at least one thiocyanate group and to the use of these compounds for the preparation of new polymers and copolymers.

Numerous acrylic and methacrylic compounds carrying groups such as halogen, hydroxyl, thiol, epoxide, etc. are already known from the scientific and industrial literature. Each of these families of compounds has already found various applications in various industries because of the ease of polymerization of the acrylic double bond. To date, however, the scientific and industrial literature has for the most part not described acrylic and methacrylic compounds carrying a thiocyanate group much less polymers thereof. Exceptions to this are found in two Russian publications, Chemical Abstracts, vol. 83, 1975, page 428, abstract 199643d and vol. 81, 1974, page 389, abstract 83548 both describing poly(thiocyanoethyl)methacrylate and the Chemical Abstracts registry handbook, number 76392-31-9 listing the thiocyanobutyl ester of methyl methacrylate.

SUMMARY OF THE INVENTION

A first object of the present invention therefore relates to providing acrylic and methacrylic compounds of the formula:

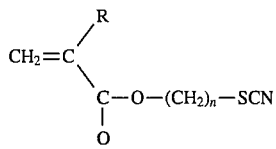

and those of formula

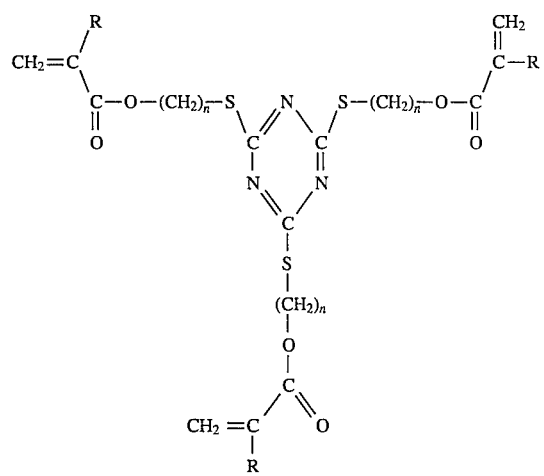

in which formulae:

n is an integer ranging from 2 to 20, and

R is a hydrogen atom, methyl or CHOHR' in which R' is straight-chain or branched alkyl radicals, optionally substituted by hydroxyl, alkoxy or ester substituents; straight-chain, branched or cyclic alkenyl radicals; aryl radicals optionally substituted by halogenated, nitro or alkoxy substituents; unsaturated heterocyclic radicals; alkylaryl; or arylalkyl, with the proviso that R in formula I does not represent methyl when n is 2 or 4.

Examples of radical R' in the compounds of formulae (I) and (II) according to the invention, when R is CHOHR', include but are not limited to methyl, ethyl, n-propyl, isopropyl, isobutyl, tert-butyl, n-pentyl, n-hexyl, n-heptyl, n-nonyl, trichloromethyl, 3-chloro-propyl, 1-propenyl, 2-methyl-2-propenyl, cyclohexenyl, phenyl, benzyl, 2-phenylethyl, parachlorophenyl, para-toluyl, para-methoxyphenyl, paranitrophenyl, ortho-chlorophenyl, styryl, methoxymethyl, 2-acetylethyl, 2-pyridyl, 3-pyridyl, 4-pyridyl, 4-quinolyl, 2-furyl, 4-methyl-2-furyl, 2-(2-furyl)-1- vinyl, 2-oxo-1-propyl, 1-ethyl 2-methanesulfonate, 1-benzyloxy-1-ethyl, 3-benzoyloxy-1-propyl, 3-benzoyloxy-1-butyl, benzyloxymethyl, 2-(2-methyl-1,3-dioxolane)-1-ethyl, 3-(tetrahydropyranyl-2-oxy)-1-propyl,

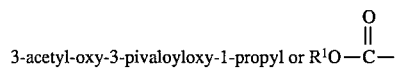

3-acetyl-oxy-3-pivaloyloxy-1-propyl or $R^1O-\overset{\overset{\displaystyle O}{\|}}{C}-$ radicals, $R^1$ being an alkyl radical having 1 to 18 carbon atoms.

A second object of the present invention is to provide a process for the preparation of the acrylic and methacrylic compounds of formulae (I) and (II). Although all of these compounds have in common for their preparation a step using a thiocyanate salt and a halogenated acrylate or methacrylate, their synthesis nevertheless has particular features depending on whether R is chosen from a hydrogen atom and a methyl radical or depending on whether R is chosen from the radicals CHOHR' as defined above. It is for this reason that the preparation process according to the invention will now be described with reference to each of the families of compounds according to the invention.

The preparation of the acrylic and methacrylic compounds of formula (I) in which R is chosen from a hydrogen atom and a methyl radical and n is an integer ranging from 2 to 20 is carried out by reacting a halogeno-n-alkyl acrylate or methacrylate with a thiocyanate salt in an organic solvent and in the presence of an effective amount of at least one phase transfer agent. The halogeno-n-alkyl (meth)acrylate which is reacted in accordance with this process has the general formula

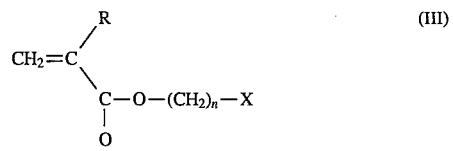

in which R and n are as defined above and X is a halogen atom. X is preferably chosen from chlorine and bromine, but may also be iodine. The halogeno-n-alkyl (meth)-acrylates of formula (III) may themselves be obtained by esterification of the (meth)acrylic acid chloride by a halogeno alcohol of formula HO—$(CH_2)_n$—X, this reaction taking place in an organic solvent such as chloroform, if necessary in the presence of a hydrochloric acid capturing agent, such as a tertiary amine.

The following may be mentioned in particular as thiocyanate salts which may be reacted with the halogeno-n-alkyl (meth)acrylate of formula (III): alkali metal thiocyanates, such as sodium thiocyanate and potassium thiocyanate, and ammonium thiocyanate. The following may be mentioned as organic solvents suitable for this reaction: ketones, such as acetone, methyl isobutyl ketone and methyl ethyl ketone, amides, such as dimethylformamide, formamide and N,N-dimethylacetamide, cycloalkane or aromatic hydrocarbons, such as cyclohexane, methylcyclohexane, benzene and toluene, alcohols, such as ethanol, nitriles, such as acetonitrile and benzonitrile, and chlorinated solvents, such as chlorobenzene, ortho-dichlorobenzene, 1,2-dichloroethane and carbon tetrachloride.

The organic solvent is used in a proportion which may vary depending on the halogeno-n-alkyl (meth)acrylate on the one hand and on the nature of the solvent on the other hand. However, the most usual are generally between 0.5 and 2.5 moles of (meth)acrylate of formula (III) per liter of organic solvent.

The reaction temperature obviously depends on the nature of the organic solvent chosen, given that the reaction is most often carried out at the reflux temperature of the said solvent. Thus, the reaction temperature is most often chosen between 50° C. and 120° C. approximately. Finally, the reaction according to the invention is carried out in the presence of at least one phase transfer agent, which may be chosen, in particular, from:

quaternary ammonium salts, such as tetra-n-butyl-ammonium chloride, bromide and iodide, tetra-n-butylammonium hydrogen sulfate, trimethylphenyl-ammonium bromide, methyltricaprylylammonium chloride, trimethylbenzylammonium and triethyl-benzylammonium chlorides, tetramethylammonium chloride and bromide and tetraethylammonium iodide, and quaternary phosphonium salts, such as methyltriphenylphosphonium bromide, tetra-n-butylphosphonium bromide and triphenyliodophosphonium iodide.

The effective amount of phase transfer agent obviously depends on the nature of the transfer agent chosen and on the substrate—(meth)acrylate of formula (III)—involved in the reaction. However, it is generally between 0.04 and 0.4 mole of transfer agent per 1 mole of substrate.

In the process according to the invention, a proportion of 1 to 2 moles approximately of thiocyanate salt per 1 mole of (meth)acrylate of formula (III) is generally used. Finally, the process may be carried out in the presence of a halide, preferably a bromide or iodide, of an alkali metal, preferably sodium or potassium. This alkali metal halide, enabling in situ replacement of halogen to be carried out in order to obtain a more reactive substrate, may be used in a proportion ranging up to 1 mole per 1 mole of (meth)acrylate of formula (III).

Although atmospheric pressure is generally satisfactory, the process according to the invention may also be carried out under reduced pressure, for example between 0.05 and 1 bar approximately.

Finally, the reaction according to the invention may be carried out in the presence of an effective amount of at least one polymerization inhibitor.

This inhibitor is used, for example, in an amount of from 0.05% to 0.5% by weight, based on (meth)acrylate. The following may be mentioned in particular as examples of polymerization inhibitors which can be used: phenothiazine, hydroquinone methyl ether, N,N-diethylhydroxylamine, nitrobenzene, di-tert-butylcatechol, hydroquinone, p-anilinophenol, di-(2-ethylhexyl)-octylphenyl phosphite and their mixtures in any proportion.

The preparation of the acrylic compounds of formula (I) in which R is chosen from the radicals CHOHR' may be carried out by reacting an acrylic compound of formula (I) in which R is a hydrogen atom—this compound being obtained as described above—with an aldehyde in the presence of an effective amount of at least one functionalization catalyst. The following may be mentioned in particular as functionalization catalysts suitable for the reaction with an aldehyde: relatively strong bases, such as cyclic tertiary amines having at least one nitrogen atom common to three rings, described in U.S. Pat. No. 3,743,669, for example diazabicyclo-[2.2.2]octane, quinuclidine and α-quinuclidinol. An effective amount of functionalization catalyst obviously depends on the nature of the latter, but also on the acrylate of formula (I) (R=H) and the aldehyde. It is generally between 0.1 and 10% approximately, preferably between 1 and 6% approximately, in moles relative to the sum of the reactants present—acrylate of formula (I) (R=H) and aldehyde.

The aldehyde with which the acrylate of formula (I) (R=H) is reacted has the general formula R'CHO, in which R' has the meaning already mentioned above. The following may be mentioned in particular as examples of such aldehydes: acetaldehyde, n-butyraldehyde, phenylacetaldehyde, benzaldehyde, crotonaldehyde, m-ethylphenylacetaldehyde, m-chlorobenzaldehyde, p-nitrophenylacetaldehyde, m-carbomethoxybenzaldehyde, p-methoxybenzaldehyde, formaldehyde, propionaldehyde, isobutyraldehyde, tert-butyraldehyde, n-pentaldehyde, n-hexaldehyde, n-heptaldehyde, n-nonaldehyde, 4-chlorobutyraldehyde, p-chlorobenzaldehyde, o-chlorobenzaldehyde, 4-cyclohexenealdehyde, furfuraldehyde, 4-methylfurfuraldehyde and the like.

The reactants—aldehyde and acrylate of formula (I) in which R is hydrogen—are generally used in a proportion of 0.5 to 2 moles of aldehyde per 1 mole of acrylate. The temperature at which the reaction is carried out is generally between 0° C. and 150° C. approximately. The reaction between the aldehyde and the acrylate may also be carried out in the presence of at least one electrophilic activator, such as a lithium salt, in particular a lithium halide such as lithium chloride. The latter may be used in an amount of up to 0.1 mol-% relative to the sum of the reactants.

Finally, this reaction according to the invention may be carried out in the presence of an effective amount of at least one polymerization inhibitor.

This inhibitor is used, for example, in an amount of from 0.05% to 0.5% by weight, based on (meth)acrylate. The following may be mentioned in particular as examples of polymerization inhibitors which can be used: phenothiazine, hydroquinone methyl ether, N,N-diethyl-hydroxylamine, nitrobenzene, di-tert-butylcatechol, hydroquinone, p-anilinophenol, di-(2-ethylhexyl)-octyl-phenyl phosphite and their mixtures in any proportion.

The preparation of the acrylic compounds of formula (I) in which R is chosen from the radicals CHOHR' may also take place by first reacting a halogeno-n-alkyl acrylate of formula (III) with an aldehyde of formula R'CHO in the presence of an effective amount of at least one functionalization catalyst in order to obtain an intermediate of formula:

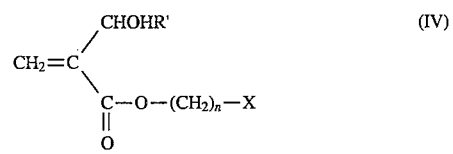

and then, in a second step, reacting the said intermediate with a thiocyanate salt in an organic solvent and in the presence of an effective amount of at least one phase transfer agent. The operating conditions for the first step of this process, in particular the nature of the functionalization catalyst, the reaction temperature and the proportions of the various reactants, are analogous to those described above with regard to the first preparation process. The operating conditions for the second step of the process, in particular the nature of the organic solvent, the nature of the phase transfer agent, the reaction temperature and the proportions of the various reactants, are analogous to those described above with regard to the acrylic and methacrylic compounds of formula (I) in which R is chosen from a hydrogen atom and a methyl radical. The acrylic compounds of formula (IV) above are new synthesis intermediates. The first step of this process can, if necessary, be carried out in the presence of an effective amount of at least one electrophilic activator, such as a lithium salt, the concept of effective amount being analogous to that indicated above for the use of these compounds. This second preparation method is more particularly applicable to the compounds in which n is an integer ranging from 2 to 4.

The preparation of the acrylic and methacrylic compounds of formula (II), that is to say the trimers of the acrylic and methacrylic compounds of formula (I), may be carried out by reaction of the said compounds of formula (I) with at least one alkali metal hydride, such as lithium hydride or sodium hydride, in the presence of an organic solvent. The organic solvent used may be, in particular, an aromatic hydrocarbon, such as benzene, toluene or xylenes, or an aliphatic hydrocarbon, such as heptane. This reaction is carried out at a temperature which is generally between 50° C. and 120° C. approximately, depending on the nature of the solvent chosen. The reaction time is relatively long and generally between 2 and 80 hours approximately, depending on the reaction temperature. This reaction is generally incomplete and leads, at the end of the time mentioned above, to a mixture of the compound of formula (I) and its trimer of formula (II), from which mixture it is possible to isolate and then to purify the acrylic or methacrylic compound of formula (II). A third object of the present invention is to provide the application of the new acrylic and methacrylic compounds described above to the formulation of new polymers and copolymers. More precisely, the present invention relates to polymers and copolymers comprising at least one unit derived from at least one acrylic or methacrylic compound of formula (I) and/or (II), R, R' and n being as defined above with the provision that in the case of homopolymers, R does not represent methyl in formula (I) if at the same time n is 2. Copolymers may comprise at least one unit derived from at least one comonomer copolymerizable with the said acrylic or methacrylic compound of formula (I) and/or (II), such as, for example:

an alkyl acrylate or methacrylate in which the straight-chain or branched alkyl group, which if necessary is substituted, for example by at least one halogen atom such as chlorine or fluorine and/or by at least one hydroxyl group, has from 1 to 20 carbon atoms, an aryl acrylate or methacrylate, such as benzyl methacrylate, a vinyl-aromatic hydrocarbon, such as styrene, vinyltoluene, alpha-methylstyrene, 4-methylstyrene, 3-methylstyrene, 4-methoxystyrene, 2-hydroxymethylstyrene, 4-ethylstyrene, 4-ethoxystyrene, 3,4-dimethylstyrene, 2-chlorostyrene, 3-chlorostyrene, 4-chloro-3-methylstyrene, 3-tert-butylstyrene, 2,4-dichlorostyrene, 2,6-dichlorostyrene and 1-vinylnaphthalene, an unsaturated nitrile, such as acrylonitrile or methacrylonitrile, an N-substituted maleimide, such as N-ethylmaleimide, N-isopropylmaleimide, N-n-butylmaleimide, N-isobutylmaleimide, N-tert-butylmaleimide, N-n-octylmaleimide, N-cyclohexylmaleimide, N-benzylmaleimide and N-phenylmaleimide, an unsaturated dicarboxylic acid anhydride, such as maleic anhydride, itaconic anhydride, citraconic anhydride or tetrahydrophthalic anhydride, acrylic or methacrylic acid, a polyol acrylate or methacrylate, such as the diacrylates and dimethacrylates of ethylene glycol, propylene glycol, butane-1,3-diol, butane-1,4-diol, hexane-1,6-diol, neopentyl glycol, cyclohexane--1,4-diol, cyclohexane-1,4-dimethanol, 2,2,4-tri-methylpentane-1,3-diol, 2-ethyl-2-methylpropane-1,3-diol, 2,2-diethylpropane-1,3-diol, diethylene glycol, dipropylene glycol, triethylene glycol, tripropylene glycol, tetraethylene glycol, tetrapropylene glycol, trimethylolethane, trimethylolpropane, glycerol and pentaerythritol, the triacrylates and trimethacrylates of trimethylolethane, trimethylolpropane, glycerol and pentaerythritol, pentaerythritol tetraacrylates and tetramethacrylates, dipentaerythritol di(meth)acrylates to hexa(meth)acrylates, the poly(meth)acrylates of mono- or poly-ethoxylated or mono- or polypropoxylated polyols, such as triethoxylated trimethylolpropane triacrylate and trimethacrylate and tripropoxylated trimethylolpropane triacrylate and trimethacrylate; tripropoxylated glycerol triacrylate and trimethacrylate; and tetraethoxylated pentaerythritol triacrylate, trimethacrylate, tetraacrylate and tetramethacrylate, an epoxy acrylate or methacrylate chosen from 2-epoxyethylbicyclo[2.2.1]hept-5(6)-yl (meth)acrylate, epoxydicyclopentyloxyethyl acrylate and those of formula:

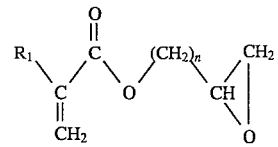

in which $R_1$ is chosen from a hydrogen atom and a methyl radical and n is an integer ranging from 1 to 16, those of formula

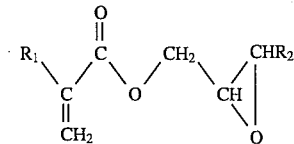

in which $R_1$ is chosen from a hydrogen atom and a methyl radical and $R_2$ is chosen from alkyl radicals having 1 to 12 carbon atoms and aryl radicals having from 6 to 12 carbon atoms, and those of formulae:

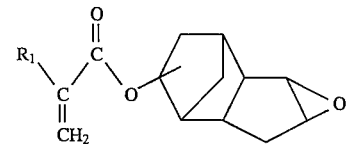

and

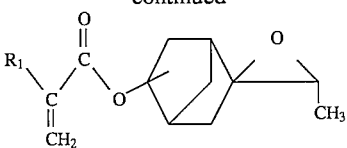

in which $R_1$ is chosen from a hydrogen atom and a methyl radical, a dialkylaminoalkyl acrylamide or methacrylamide, acrylate or methacrylate and their quaternary salts, 2-(2-norbornyloxy)ethyl acrylate and methacrylate and 2-(2-dimethanodecahydronaphthyloxy)ethyl acrylate and methacrylate, and acrylic and methacrylic oxazolidones chosen from those of formula:

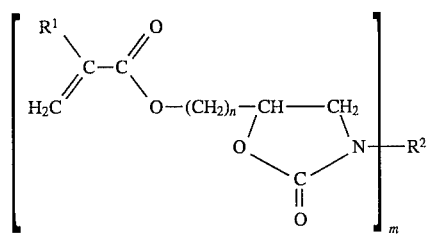

and those of formula:

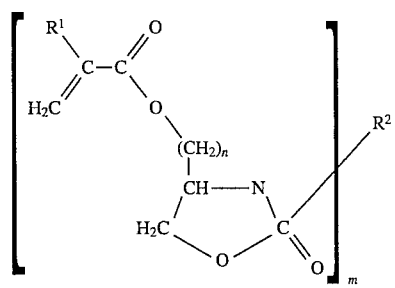

in which formulae:

$R^1$ is chosen from a hydrogen atom and a methyl radical, n is an integer ranging from 1 to 12, m is an integer ranging from 1 to 3, and $R^2$ is a straight-chain, branched or cyclic alkyl hydrocarbon radical or an aromatic hydrocarbon radical having from 5 to 12 carbon atoms, it being possible for the said oxazolidones to be obtained by reaction, at between 30° C. and 90° C., of a compound carrying a (meth)acrylic group with a compound carrying at least one isocyanate group, acrylic and methacrylic compounds chosen from those of formula

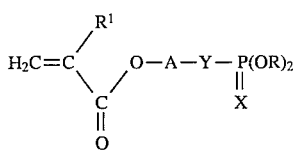

in which $R^1$ is chosen from a hydrogen atom and a methyl radical,

A is chosen from the radicals $(CH_2)_n$ for which n is an integer from 2 to 12 and the radical $-(CH_2CH_2O)_d-CH_2CH_2-$, d being an integer ranging from 1 to 20, X is chosen from sulfur and oxygen atoms, Y is chosen from sulfur and oxygen atoms, on condition that X is a sulfur atom and Y is an oxygen atom when A is the radical $-(CH_2CH_2O)_d-CH_2CH_2-$, and R is chosen from alkyl radicals having from 1 to 20 carbon atoms and the groups $-(CH_2)_pSR^3$ in which p is an integer ranging from 3 to 12 and $R^3$ is an alkyl radical having from 1 to 20 carbon atoms, those of formula:

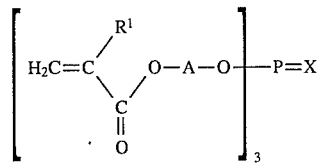

in which:

$R^1$ is chosen from a hydrogen atom and a methyl radical,

A is chosen from the radicals $(CH_2)_n$ for which n is an integer from 2 to 12 and the radical $-(CH_2CH_2O)_d-CH_2CH_2-$, d being an integer ranging from 1 to 20, and X is chosen from sulfur and oxygen atoms, and those of formula:

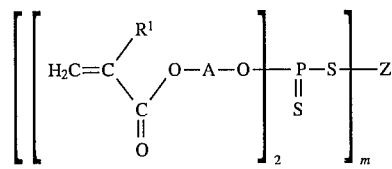

in which:

$R^1$ is chosen from a hydrogen atom and a methyl radical,

A is chosen from the radicals $(CH_2)_n$ for which n is an integer from 2 to 12, m is an integer ranging from 1 to 3, and Z is chosen from a hydrogen atom, the radicals $R^2QH$, $R^2$ being an alkyl radical having from 2 to 12 carbon atoms and Q being chosen from oxygen and sulfur atoms, and the atoms of the metals of groups IA, IIA, IIIA, IB, IIB, VIB, VIIB and VIII of the Periodic Classification, on condition that Z is chosen from a hydrogen atom and the radicals $R^2OH$ when m=1 and that m is the valency of Z when Z is a metal.

Compounds of this type may be prepared by reaction of an acrylic or methacrylic compound of formula:

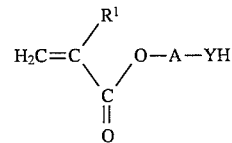

in which $R^1$, A and Y have the same meanings as in formula (X), with a pentavalent phosphorus compound, which latter may be, for example, a compound of formula $PXT_3$ in which X has the same meaning as in the formula (X) and T denotes a halogen atom, or a phosphorus compound of formula:

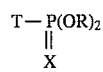

in which R and X have the same meanings as in formula (I) and T denotes a halogen atom, or the pentasulfide $P_2S_5$, acrylic and methacrylic compounds chosen from those of formula:

$$H_2C=C\underset{\underset{O}{\overset{\|}{C}}}{\overset{R^1}{\diagup}}\diagdown O-R^2-\underset{XH}{\overset{|}{CH}}-CHR^6-S-\underset{S}{\overset{\|}{P}}-(OR^3)_2 \quad (XI)$$

and those of formula:

$$H_2C=C\underset{\underset{O}{\overset{\|}{C}}}{\overset{R^1}{\diagup}}\diagdown O-R^2-\underset{\underset{R^6}{\overset{|}{CHXH}}}{\overset{|}{CH}}-S-\underset{S}{\overset{\|}{P}}-(OR^3)_2$$

in which formulae:

$R^1$ is chosen from a hydrogen atom and a methyl radical,

X is a heteroatom chosen from oxygen and sulfur, $R^2$ is chosen from straight-chain or branched alkylene, monocyclic or polycyclic cycloalkylene and heterocycloalkylene and alkylarylene and arylalkylene groups comprising from 1 to 12 carbon atoms, $R^6$ is chosen from a hydrogen atom and alkyl and aryl radicals having from 1 to 12 carbon atoms, and $R^3$ is chosen from alkyl and aryl radicals having 1 to 20 carbon atoms, the groups —$(CH_2)_pSR^4$ in which p is an integer ranging from 2 to 12 and $R^4$ is an alkyl radical having from 1 to 20 carbon atoms or a monocyclic or polycyclic cycloalkyl group having from 4 to 10 carbon atoms, each ring of the said group comprising from 4 to 6 members, and the groups $$-(CH_2)_q-O-\underset{\underset{O}{\overset{\|}{}}}{C}-\underset{\overset{|}{R^5}}{C}=CH_2$$

in which q is an integer ranging from 2 to 12 and $R^5$ is chosen from a hydrogen atom and a methyl radical. Such compounds may be prepared by reaction of an acrylic or methacrylic epoxide or episulfide of formula:

$$H_2C=C\underset{\underset{O}{\overset{\|}{C}}}{\overset{R^1}{\diagup}}\diagdown O-R^2-\underset{X}{\overset{}{CH-CHR^6}}$$

in which $R^1$ $R^2$ $R^6$ and X have the same meanings as in formula (XI), with a thiophosphorus compound of formula:

$$(R^3O)_2-\underset{S}{\overset{\|}{P}}-SH.$$

Polymers and copolymers of this type are obtained by (co)polymerizing at least one acrylic or methacrylic compound of formula (I) and/or (II) and, optionally, at least one cooplymerizable comonomer, as defined above, in the presence of at least one free radical initiator, such as a peroxide, a hydroperoxide or a diazo compound. The (co)polymerization is generally carried out at a temperature of between 50° C. and 120° C. approximately and using one of the monomers as solvent. It may also take place in emulsion in water, at a temperature of between 50° C. and 100° C., in the presence of at least one surface-active agent.

The polymers and copolymers of this invention can be formed into shaped articles of manufacture by conventional processes, e.g., molding, casting, extrusion, spinning, etc. They can also be used as vehicles for protective coatings and as binders. In general, they can be used in the same manner as other poly(meth)acrylates.

BRIEF DESCRIPTION OF THE DRAWINGS

Various other objects, features and attendant advantages of the present invention will be more fully appreciated as the same becomes better understood when considered in conjunction with the accompanying drawings, in which like reference characters designate the same or similar parts throughout the several views, and wherein:

All the figures relate to H NMR, IR and $^{13}C$ NMR characteristics of specific compounds as explained in detail in the examples.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire disclosures of all applications, patents and publications, cited above and below, and of corresponding application French Appln. No. 90 08698, filed Jul. 9, 1990, are hereby incorporated by reference.

EXAMPLES

Examples 1 to 5

Potassium thiocyanate (2 mols) is reacted with 2-chloroethyl acrylate (1 mol) at 65° C. in methyl ethyl ketone in the presence of tetra-n-butylammoniumiodide as phase transfer agent and, if necessary, in the presence of potassium iodide. The number of moles of each of the last two compounds mentioned is indicated in Table I below, as is the reaction time t (expressed in hours) and the yield Y of 2-thiocyanatoethyl acrylate, expressed as a percentage and obtained after isolation and purification on silica gel. The 2-thiocyanatoethyl acrylate was also identified by the following techniques:

proton nuclear magnetic resonance, using a JEOL PMX60SI spectrometer: the spectrum obtained comprises two triplets at 3.25 ppm (2H) and 4.40 ppm (2H) and a multiplet at 6.2 ppm (3H)

Infrared spectrophotometry, using a PERKIN ELMER 841 spectrometer: the spectrum obtained comprises characteristic bands at 2957, 2157, 1727, 1638, 1620, 1409 and 1183 $cm^{-1}$ (appended FIG. 2).

Carbon 13 nuclear magnetic resonance, using a BRUKER AC 200 spectrometer:

TABLE I

| Example | 1 | 2 | 3 | 4 | 5 |
|---|---|---|---|---|---|
| $(C_4H_9)_4NI$ | 0.1 | 0.2 | 0.2 | 0.2 | 0.3 |
| KI | 0.1 | 0 | 0.1 | 0.5 | 0.1 |

TABLE I-continued

| Example | 1 | 2 | 3 | 4 | 5 |
|---|---|---|---|---|---|
| t | 72 | 120 | 63 | 63 | 48 |
| y | 62 | 81 | 79 | 78 | 76 |

Examples 6 to 11

The operating method of Example 3 is repeated, replacing tetra-n-butylammonium iodide by another phase transfer agent, the nature of which is specified in Table II below, as is the reaction time t and the yield Y (%).

TABLE II

| Example | Phase transfer agent | t | Y |
|---|---|---|---|
| 6 | $(C_4H_9)_4NHSO_4$ | 75 | 55 |
| 7 | $(C_4H_9)_4NBr$ | 75 | 71 |
| 8 | $(C_4H_9)_4NCl$ | 72 | 72 |
| 9 | $(C_6H_5)_3CH_3PBr$ | 84 | 90 |
| 10 | $(CH_3)_3C_6H_5NBr$ | 120 | 73 |
| 11 | $CH_3N[(CH_2)_7CH_3]Cl$ | 144 | 52 |

Example 12

The operating method of Example 7 is repeated, replacing potassium iodide by an equivalent amount of potassium bromide. After a reaction time of 113 hours at 65° C., 2-thiocyanatoethyl acrylate is obtained in a yield of 78%.

Examples 13 to 20

The operating method of Example 9 is repeated, replacing methyl ethyl ketone by another solvent, the nature of which is specified in Table III below, and correlatively modifying the reaction temperature T (expressed in degrees Celsius). Table III below also indicates the reaction time and the yield Y (expressed as a percentage) of 2-thiocyanatoethyl acrylate in each case.

TABLE III

| Example | Solvent | T | t | y |
|---|---|---|---|---|
| 13 | dimethylformamide | 65 | 48 | 68 |
| 14 | ethanol | 65 | 120 | 52 |
| 15 | acetonitrile | 65 | 72 | 76 |
| 16 | benzonitrile | 65 | 120 | 76 |
| 17 | N,N'-dimethyl-acetamide | 65 | 42 | 90 |
| 18 | toluene | 90 | 72 | 73 |
| 19 | methylisobutyl-ketone | 69 | 96 | 70 |
| 20 | acetone | 56 | 168 | 64 |

Examples 21 to 35

The operating method of Example 9 is repeated, replacing 2-chloroethyl acrylate by a halogeno-n-alkyl acrylate or methacrylate of formula (III) in an equivalent amount. A thiocyanato-n-alkyl acrylate or methacrylate of formula (I) is thus obtained, which is identified by the same techniques as those mentioned in Examples 1 to 5 with respect to 2-thiocyanatoethyl acrylate. Table IV below collates, as a function of the value of n, the meaning of R and X in the formula (III) and the reaction time t (expressed in hours), the yield Y in which the said product is obtained, numbers of the figures appended reproducing the proton nuclear magnetic resonance ($^1$H NMR), carbon 13 nuclear magnetic resonance ($^{13}$C NMR) and infrared (IR) spectra of the product obtained.

These spectra have common characteristics and may be described as follows:

Proton Nuclear Magnetic Resonance: signal (δ) m, 1H m, 1H t, 2H t, 2H m, 3H (2n–4)H R=CH$_3$, n=2 6.20 5.65 4.45 3.3 2.0 R=CH$_3$, n>2 6.05 5.35 4.15 3.0 1.9 1.0–2.0 R=H, n>2: 5.7–6.7 ppm (m, 3H), 4.15 ppm (t, 2H), 2.95 ppm (t, 2H) and 1.5–2.2 ppm (m, (2n-4)H).

Infrared Spectrophotometry: υ in cm$^{-1}$ R=CH$_3$ 2158–2154, 1723–1716, 1640–1638 R=H 2157–2154, 1727–1724, 1638–1637, 1622–1619

TABLE IV

| Example | n | Y | X | t | Y |
|---|---|---|---|---|---|
| 21 | 2 | CH$_3$ | Cl | 84 | 76 |
| 22 | 3 | H | Cl | 45 | 92 |
| 23 | 3 | CH$_3$ | Cl | 26 | 79 |
| 24 | 4 | H | Cl | 31 | 75 |
| 25 | 4 | CH$_3$ | Cl | 55 | 81 |
| 26 | 5 | H | Br | 2 | 89 |
| 27 | 5 | CH$_3$ | Br | 2 | 82 |
| 28 | 6 | H | Br | 2 | 82 |
| 29 | 6 | CH$_3$ | Br | 2 | 90 |
| 30 | 8 | H | Br | 2 | 85 |
| 31 | 8 | CH$_3$ | Br | 2 | 81 |
| 32 | 10 | H | Br | 2 | 84 |
| 33 | 10 | CH$_3$ | Br | 2 | 75 |
| 34 | 12 | H | Br | 2 | 95 |
| 35 | 12 | CH$_3$ | Br | 2 | 91 |

Example 36

1 mol of 2-chloroethyl acrylate and 0.7 mol of benzaldehyde are reacted for 24 hours at a temperature of 20° C. in the presence of 0.1 mol of diazabicyclo[2.2.2]octane and 0.1 mol of lithium chloride. 0.45 mol of acrylate of formula:

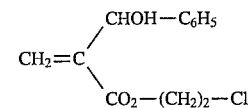

is then obtained (yield based on benzaldehyde=64%).

This acrylate, identified by the same techniques as those mentioned in Examples 1 to 5 with regard to 2-thiocyanatoethyl acrylate, has the following spectral characteristics:

Proton Magnetic Resonance: 7.25 ppm (m, 5H); 6.33 ppm (m, 1H); 5.9 ppm (m, 1H); 5.45 ppm (s, 1H); 4.25 ppm (t, 2H); 3.55 ppm (t, 2H); ppm (s, 1H), Infrared Spectrophotometry: 3472 cm$^{-1}$; 1721 cm$^{-1}$; 1630 cm$^{-1}$, Carbon 13 Magnetic Resonance: 165.60 ppm; 141.73 ppm; 141.16 ppm; 128.61 ppm; 128.37 ppm; 127.81 ppm; 126.56 ppm; 72.92 ppm; 64.21 ppm; 41.22 ppm.

Example 37

0.2 mol of the acrylate prepared in Example 36 is reacted with 0.4 mol of potassium thiocyanate for 168 hours at 65° C. in 200 ml of methyl ethyl ketone, in the presence of 0.04 mol of methyltriphenylphosphonium bromide and 0.02 mol of potassium iodide. 0.148 mol of acrylate of formula:

$$CH_2=C \overset{\displaystyle CHOH-C_6H_5}{\underset{\displaystyle CO_2-(CH_2)_2-SCN}{}}$$

is then obtained (yield based on the acrylate=74%).

This acrylate, identified by the same techniques as those mentioned in Examples 1 to 5 with regard to 2-thiocyanatoethyl acrylate, has the following spectral characteristics:

Proton Magnetic Resonance: 7.25 ppm (m, 5H); 6.35 ppm (m, 1H); 5.9 ppm (m, 1H); 5.5 ppm (m, 1H); 4.35 ppm (t, 2H); 3.05 ppm (t, 2H); 3 ppm (s, 1H), Infrared spectrophotometry: 3484 $cm^{-1}$; 2157 $cm^{-1}$; 1721 $cm^{-1}$; 1630 $cm^{-1}$, Carbon 13 Magnetic Resonance: 165.48 ppm; 141.44 ppm; 141.15 ppm; 128.44 ppm; 127.92 ppm; 127.16 ppm; 126.63 ppm; 111.24 ppm; 72.77 ppm; 62.29 ppm; 32.50 ppm.

Example 38

0.5 mol of 2-thiocyanatoethyl acrylate obtained in accordance with Example 9 is reacted with 0.35 mol of benzaldehyde for 48 hours at a temperature of 20° C., in the presence of 0.05 mol of diazabicyclo[2.2.2]octane and 0.05 mol of lithium chloride. 0.231 mol of the same product, identified by its infrared and nuclear magnetic resonance spectral characteristics, as that obtained in Example 37 is then obtained. (Yield based on benzaldehyde: 66%).

Example 39

0.3 mol of 2-thiocyanatoethyl methacrylate obtained in accordance with Example 21 is reacted with 0.1 mol of sodium hydride at 55° C. for 24 hours in 400 ml of toluene. By monitoring the progress of the reaction by gas phase chromatography, the production of a mixture consisting of 75% of 2-thiocyanatoethyl methacrylate and 25% of its trimer of formula (II) is then observed, the trimer being identified in the following way:

a) Proton Nuclear Magnetic Resonance:

Except for the peaks at 6.2 ppm (m, 1H) at 5.65 ppm (m, 1H), at 4.5 ppm (t, 2H) and at 2 ppm (m, 3H), the chemical shifts of which are retained, the spectrum indicates the presence of a triplet at 3.05 ppm (2H).

b) Infrared Spectrophotometry The spectrum indicates the presence of a new characteristic band at 2096 $cm^{-1}$.

Example 40

The operating method of Example 39 is repeated except for the amount of sodium hydride, which is increased to 0.3 mol, and the reaction time, which is brought to 72 hours. A mixture of 47% of 2-thiocyanatoethyl methacrylate and 53% of its trimer of formula (II), identified as above, is then obtained.

Example 41

The operating method of Example 39 is repeated except for the amount of sodium hydride, which is increased to 0.9 mol, and the reaction time, which is brought to 72 hours. A mixture of 80% of 2-thiocyanatoethyl methacrylate and 20% of its trimer of formula (II), identified as above, is then obtained.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A process for the preparation of an acrylic or methacrylic compound of formula (I):

$$CH_2=C \overset{\displaystyle R}{\underset{\displaystyle \underset{\displaystyle O}{\overset{\displaystyle \|}{C}}-O-(CH_2)_n-SCN}{}} \qquad (I)$$

wherein R is a hydrogen atom or methyl and n is an integer ranging from 2 to 20 inclusive, comprising reacting a halogeno-n-alkyl acrylate or methacrylate of the formula:

$$CH_2=C \overset{\displaystyle R}{\underset{\displaystyle \underset{\displaystyle O}{\overset{\displaystyle \|}{C}}-O-(CH_2)_n-X}{}} \qquad (III)$$

in which n is as defined above and X is a halogen atom, with a thiocyanate salt in an organic solvent and in the presence of an effective phase-transferring amount of at least one phase transfer agent.

2. A process for the preparation of an acrylic or methacrylic compound of formula (I) according to claim 1, wherein the thiocyanate salt is an alkali metal thiocyanate or an ammonium thiocyanate.

3. A process for the preparation of an acrylic or methacrylic compound of formula (I) according to claim 1, wherein the organic solvent for the reaction between the thiocyanate salt and the acrylate of formula (III) is a ketone, amide, cycloalkane, aromatic hydrocarbon, alcohol or nitrile.

4. A process for the preparation of an acrylic or methacrylic compound of formula (I) according to claim 1, wherein the phase transfer agent is a quaternary ammonium salt, quaternary phosphonium salt or a quaternary arsonium salt.

5. A process for the preparation of an acrylic or methacrylic compound of formula (I) according to claim 2, wherein the phase transfer agent is a quaternary ammonium salt, quaternary phosphonium salt or a quaternary arsonium salt.

6. A process for the preparation of an acrylic or methacrylic compound of formula (I) according to claim 3, wherein the functionalization catalyst is a cyclic tertiary amine having at least one nitrogen atom common to three rings.

7. A process for the preparation of an acrylic or methacrylic compound of formula (I) according to claim 5, wherein the functionalization catalyst is a cyclic tertiary amine having at least one nitrogen atom common to three rings.

* * * * *